United States Patent [19]

Endo et al.

[11] 4,137,322
[45] Jan. 30, 1979

[54] ML-236B CARBOXYLIC ACID DERIVATIVES AND THEIR USE AS ANTIHYPERLIPEMIC AGENTS

[75] Inventors: Akira Endo; Akira Terahara; Noritoshi Kitano; Akira Ogiso; Seiji Mitsui, all of Tokyo, Japan

[73] Assignee: Sankyo Company Limited, Tokyo, Japan

[21] Appl. No.: 847,044

[22] Filed: Oct. 31, 1977

[30] Foreign Application Priority Data

Nov. 2, 1976 [JP] Japan .................................. 51-132044
Dec. 29, 1976 [JP] Japan .................................. 51-160052
Aug. 8, 1977 [JP] Japan .................................. 52-94807

[51] Int. Cl.² ...................... C07C 69/74; C07C 69/30; A61K 31/215
[52] U.S. Cl. ........................... 424/273 R; 260/448 R; 548/344; 560/119; 560/251; 560/256; 424/305; 424/287; 424/311
[58] Field of Search ...................... 560/119, 251, 256; 260/448 R; 424/273 R, 305, 311, 287; 548/344

[56] References Cited
U.S. PATENT DOCUMENTS

3,983,140 9/1976 Endo ................................. 260/343.5

*Primary Examiner*—Robert Gerstl

*Attorney, Agent, or Firm*—Flynn & Frishauf

[57] ABSTRACT

ML-236B carboxylic acid derivatives having the formula

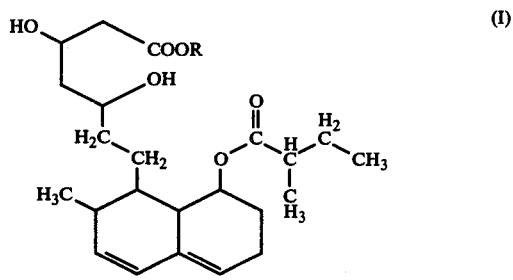

(I)

wherein R represents an alkyl group, a benzyl group optionally substituted with alkyl, alkoxy or halogen or a phenacyl group optionally substituted with alkyl, alkoxy or halogen; a group of 1/n M in which M represents a metal and n represents a valency of said metal; or a group of AH⁺ in which A represents an amino acid. These derivatives are derived from ML-236B by conventional procedures and have an antihyperlipemic activity.

16 Claims, No Drawings

ML-236B CARBOXYLIC ACID DERIVATIVES AND THEIR USE AS ANTIHYPERLIPEMIC AGENTS

This invention relates to a novel group of ML-236B carboxylic acid derivatives and their use as antihyperlipemic agents.

More particularly, it is concerned with an ML-236B carboxylic acid derivative having the formula

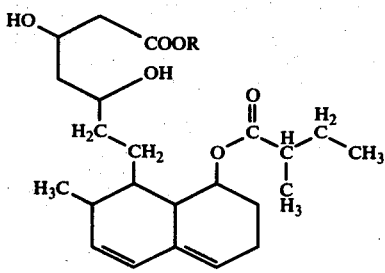

wherein R represents an alkyl group, a benzyl group optionally substituted with alkyl, alkoxy or halogen or a phenacyl group optionally substituted with alkyl, alkoxy or halogen; a group of 1/n M in which M represents a metal and n represents a valency of said metal; or a group of $AH^+$ in which A represents an amino acid. Also, it relates to a new use of the ML-236B carboxylic acid derivatives (I) as an agent for the treatment of hyperlipemia.

Heretofore, it was disclosed and claimed in Japanese Patent Application Provisional Publication No. 155690/1975 (which was laid open to public on Dec. 16, 1975 and corresponds to U.S. Pat. No. 3,983,140; British Pat. No. 1453425; Belgian Pat. No. 830033; and West German Laying Open Specification No. 2524355) that the compound having the following chemical structure, i.e., "ML-236B" itself can be prepared by cultivation of *Penicillium citrinum* SANK 18767 and exhibits a pharmacological activity as hypocholesteremic and hypolipemic medicaments.

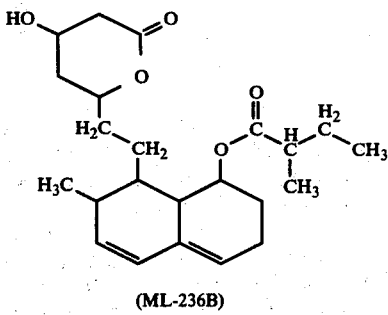

(ML-236B)

As a result of further studies made by the present inventors, it has been found that the ML-236B carboxylic acid derivative (I) can be easily derived from ML-236B itself and show a unexpectedly higher biological activity against hyperlipemia as compared with ML-236B and, therefore, the present invention has been completed upon this finding.

It is a principal object of this invention to provide the new ML-236B carboxylic acid derivatives (I) which possess a valuable activity as antihyperlipemic agents.

Another object of this invention is to provide a composition for the treatment of hyperlipemia which comprises the ML-236B carboxylic acid derivative (I) as an active ingredient.

These and other objects of this invention will be apparent to those skilled in the art from the following description.

According to one aspect of this invention, there is provided a new class of the ML-236B carboxylic acid derivatives having the above formula (I). The ML-236B carboxylic acid derivatives (I) of this invention include, more specifically, (a) esters of ML-236B carboxylic acid of the formula (I) wherein R represents an alkyl group, a benzyl group optionally substituted with alkyl, alkoxy or halogen or a phenacyl group optionally substituted with alkyl, alkoxy or halogen; (b) metal salts of ML-236B carboxylic acid of the formula (I) wherein R represents a group of 1/n M in which M represents a metal and n represents a valency of said metal; and (c) amino acid salts of ML-236B carboxylic acid of the formula (I) wherein R represents a group of $AH^+$ in which A represents an amino acid.

In the esters of ML-236B carboxylic acid, R may be exemplified by an alkyl group, preferably of 1 to 6 carbon atoms, such as methyl, ethyl, n-propyl, isopropyl, n-butyl, n-hexyl etc; a benzyl group optionally substituted with an alkyl group, an alkoxy group or a halogen atom such as benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4-chlorobenzyl, 2-bromobenzyl, 3-bromobenzyl, 4-bromobenzyl etc; or a phenacyl group optionally substituted with an alkyl group, an alkoxy group or a halogen atom such as phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-chlorophenacyl, 3-chlorophenacyl, 4-chlorophenacyl, 2-bromophenacyl, 3-bromophenacyl, 4-bromophenacyl etc. The ML-236B carboxylic acid esters are new substances and can be easily prepared according to any conventional methods, for example, by one of the following processes.

(1) Reaction of ML-236B with an alcohol wherein an inorganic acid such as hydrochloric acid, sulfuric acid etc, a boron fluoride or an acidic ion exchange resin may be employed as a catalyst and the same alcohol or any other solvents that do not participate in the reaction, e.g., chloroform, benzene and ether can be employed as a solvent.

(2) Reaction of a metal salt of ML-236B carboxylic acid with an alkyl halide (the metal salt of ML-236B carboxylic acid can be prepared by saponification of ML-236B with a weak alkali) wherein dimethylformamide, tetrahydrofuran, dimethylsulfoxide or acetone may be employed as a solvent.

(3) Reaction of ML-236B carboxylic acid with an alcohol in the same manner as the above Process (1). (ML-236B carboxylic acid can be prepared by neutralization of a metal salt of ML-236B carboxylic acid).

The ML-236B carboxylic acid metal salts are also new substances and can be prepared according to any conventional methods, for example, by saponification of ML-236B with a weak alkali.

As the ML-236B metal salts, there may be mentioned alkali metal salts, e.g., sodium or potassium salt, alkaline earth metal salts, e.g., calcium or magnesium salt, aluminum salt, iron salt, zinc salt, copper salt, nickel salt, cobalt salt and the like. Among others, alkali metal salts, alkaline earth metal salts and aluminum salt are preferable and sodium salt, calcium salt and aluminum salt are most preferable.

The ML-236B carboxylic acid.amino acid salts are novel compounds and can be prepared, for example, by contacting ML-236B with an amino acid.

As the ML-236B carboxylic acid.amino acid salt, there may be preferably mentioned those salts with a basic amino acid such as arginine, lysine, histidine, α,γ-diaminobutyric acid, ornithine and the like.

The ML-236B carboxylic acid derivatives (I) can inhibit biosynthesis of cholesterol in liver similarly as ML-236B itself does. However, a much more potent activity is available with the said derivatives as compared with that of ML-236B. Such a potent inhibitory action of cholesterol biosynthesis of ML-236B carboxylic acid derivatives is not expected upon the action of ML-236B itself. Accordingly, ML-236B carboxylic acid derivatives are very effective as an antihyperlipemia.

An inhibition activity of cholesterol biosynthesis, a lowering activity of serum cholesterol, an effective dose and a toxicity of the ML-236B carboxylic acid derivative (I) are illustrated hereinbelow.

(1) Inhibition activity of cholesterol biosynthesis

The ML-236B carboxylic acid derivatives have been found to specifically inhibit 3-hydroxy-3-methylglutaryl-CoA reductase, which is known as a rate-limiting enzyme during the biosynthesis of cholesterol. Inhibition activity of cholesterol biosynthesis [determined according to the method disclosed in J. Biol. Chem., 234, 2835 (1959)] and inhibition activity on 3-hydroxy-3-methylglutaryl-CoA reductase [determined according to the method disclosed in Anal. Biochem., 31, 383 (1969)] of these compounds are summarized in Table 1.

Table 1

| Test Compound R | Inhibition of cholesterol biosynthesis and 3-hydroxy-3-methylglutaryl-CoA reductase | |
|---|---|---|
| | Concentration to inhibit 50% of cholesterol biosynthesis (μg/ml) | Concentration to inhibit 50% of 3-hydroxy-3-methylglutaryl-CoA reductase (μg/ml)* |
| methyl | 0.01 | 0.15 |
| ethyl | 0.01 | 0.16 |
| isopropyl | 0.04 | 0.16 |
| n-butyl | 0.02 | 0.16 |
| n-hexyl | 0.02 | 0.18 |
| benzyl | 0.01 | 0.2 |
| 4-methylbenzyl | 0.01 | 0.2 |
| 4-methoxybenzyl | 0.01 | 0.2 |
| 4-chlorobenzyl | 0.01 | 0.2 |
| phenacyl | 0.01 | 0.2 |
| 4-methylphenacyl | 0.01 | 0.2 |
| 4-methoxyphenacyl | 0.01 | 0.2 |
| 4-bromophenacyl | 0.01 | 0.2 |
| Na | 0.006 | 0.16 |
| Ca | 0.006 | 0.16 |
| Al | 0.006 | 0.16 |
| Arginine | 0.007 | 0.18 |
| Lysine | 0.006 | 0.16 |
| ML-236B | 0.01 | 4.8 |

*Employed as an enzyme microsome of rat liver.

Namely, ML-236B carboxylic acid esters have an approximately equivalent inhibition effect of cholesterol biosynthesis as compared with ML-236B, while ML-236B metal salts show about 2 times stronger inhibition activity of cholesterol biosynthesis and 30 times stronger inhibition activity of 3-hydroxy-3-methylglutaryl-CoA reductase as compared with those of ML-236B.

(2) Dose and administration

A lowering activity of blood cholesterol in beagle dogs (a body weight of about 10 kg) was assayed on ML-236B carboxylic acid derivatives (I). The test was to orally administer an encapsulated test sample twice per day, in the morning (9 o'clock) and evening (16 o'clock), for continuous 5 days, collect a blood sample in the morning after 5 days and determine a total cholesterol level in serum by a conventional method. The results are shown in Table 2.

Table 2

| Test Compound R | Lowering activity of blood cholesterol in beagle dogs | |
|---|---|---|
| | Dose (mg/kg/day) | Lowering rate of total serum cholesterol (%) |
| methyl | 25 | 12 |
| | 100 | 26 |
| ethyl | 25 | 13 |
| | 100 | 19 |
| isopropyl | 25 | 19 |
| | 100 | 30 |
| n-butyl | 25 | 32 |
| | 100 | 46 |
| n-hexyl | 25 | 17 |
| | 100 | 29 |
| benzyl | 25 | 24 |
| | 100 | 38 |
| 4-methylbenzyl | 25 | 30 |
| | 100 | 41 |
| 4-methoxybenzyl | 25 | 26 |
| | 100 | 36 |
| 4-chlorobenzyl | 25 | 20 |
| | 100 | 36 |
| phenacyl | 25 | 32 |
| | 100 | 42 |
| 4-methylphenacyl | 25 | 20 |
| | 100 | 33 |
| 4-methoxyphenacyl | 25 | 26 |
| | 100 | 39 |
| 4-bromophenacyl | 25 | 21 |
| | 100 | 30 |
| Na | 25 | 24 |
| | 100 | 47 |
| Ca | 25 | 28 |
| | 100 | 44 |
| Al | 25 | 26 |
| | 100 | 41 |
| Arginine | 25 | 26 |
| | 100 | 45 |
| Lysine | 25 | 24 |
| | 100 | 44 |
| ML-236B | 25 | <5 |
| | 100 | 19 |

It is apparent that the ML-236B carboxylic acid derivatives (I) have a several times stronger activity in lowering of blood cholesterol as compared with ML-236B.

A lowering activity of blood cholesterol in rats was assayed on rats. The test was to orally administer a test sample suspended in water, collect a blood sample after 18 hours and determine a cholesterol level in serum by a conventional method.

The results are shown in Table 3.

Table 3

| Test Compound R | Lowering activity of blood cholesterol in rats | |
|---|---|---|
| | Dose (mg/kg) | Lowering rate of serum cholesterol (%) |
| methyl | 5 | 18 |
| | 20 | 23 |
| ethyl | 5 | 19 |
| | 20 | 25 |
| isopropyl | 5 | 16 |
| | 20 | 25 |

Table 3-continued

Lowering activity of blood cholesterol in rats

| Test Compound R | Dose (mg/kg) | Lowering rate of serum cholesterol (%) |
|---|---|---|
| n-butyl | 5 | 20 |
|  | 20 | 26 |
| n-hexyl | 5 | 14 |
|  | 20 | 23 |
| n-benzyl | 5 | 14 |
|  | 20 | 24 |
| 4-methylbenzyl | 5 | 13 |
|  | 20 | 26 |
| 4-methoxybenzyl | 5 | 17 |
|  | 20 | 20 |
| 4-chlorobenzyl | 5 | 15 |
|  | 20 | 21 |
| phenacyl | 5 | 14 |
|  | 20 | 21 |
| 4-methylphenacyl | 5 | 14 |
|  | 20 | 19 |
| 4-methoxyphenacyl | 5 | 14 |
|  | 20 | 23 |
| 4-bromophenacyl | 5 | 17 |
|  | 20 | 24 |
| Na | 5 | 20.6 |
|  | 20 | 23.1 |
| Ca | 5 | 16.5 |
|  | 20 | 20.9 |
| Al | 5 | 18.3 |
|  | 20 | 22.1 |
| Arginine | 5 | 19.6 |
|  | 20 | 24.1 |
| Lysine | 5 | 16.9 |
|  | 20 | 23.8 |
| ML-236B | 5 | 11.2 |
|  | 20 | 17.1 |

It is apparent that the ML-236B carboxylic acid derivatives (I) have a very satisfactory activity in lowering of blood cholesterol as compared with ML-236B.

(3) Acute toxicity

Acute toxicity of ML-236B carboxylic acid derivatives (I) was determined in oral and intraperitoneal administration (both as an aqueous suspension). The results are shown in Table 4.

Table 4-(1)

Acute toxicity

| Test Compound R | Mouse i.p. LD$_{50}$ (mg/kg) | Rat P.O. LD$_{50}$ (mg/kg) |
|---|---|---|
| methyl | >500 | >2,000 |
| ethyl | >500 | >2,000 |
| isopropyl | >500 | >2,000 |
| n-butyl | >500 | >2,000 |
| n-hexyl | >500 | >2,000 |
| n-benzyl | >500 | >2,000 |
| 4-methylbenzyl | >500 | >2,000 |
| 4-methoxybenzyl | >500 | >2,000 |
| 4-chlorobenzyl | >500 | >2,000 |
| phenacyl | >500 | >2,000 |
| 4-methylphenacyl | >500 | >2,000 |
| 4-methoxyphenacyl | >500 | >2,000 |
| 4-bromophenacyl | >500 | >2,000 |

Table 4-(2)

Acute toxicity

| Compound | Animal | Administration | LD$_{50}$ (mg/kg) |
|---|---|---|---|
| ML-236B Na salt | Mouse | p.o. | >2,000 |
|  |  | i.p. | > 500 |
|  | Rat | p.o. | >2,000 |
|  |  | i.p. | > 500 |
| "Ca salt | Mouse | p.o. | >2,000 |
|  |  | i.p. | > 500 |
|  | Rat | p.o. | >2,000 |
| "Al salt | Mouse | i.p. | > 500 |
|  |  | p.o. | >2,000 |
|  | Rat | i.p. | > 500 |
|  |  | p.o. | >2,000 |
| Arginine salt | Mouse | i.p. | > 500 |
|  |  | p.o. | >5,000 |
|  | Rat | i.p. | > 500 |
|  |  | p.o. | >5,000 |
| Lysine salt | Mouse | i.p. | > 500 |
|  |  | p.o. | >5,000 |
|  | Rat | p.o. | >5,000 |
|  |  | i.p. | > 500 |

As apparent from the above-recited experiments, ML-236B carboxylic acid derivatives can be administered orally, through intravenous injection or the like manner and their effects are distinctly far more superior to ML-236B. A dose for the treatment of an adult may vary depending upon administration route and frequency, but it is usually within the range of 100–3000 mg per day, preferably 1500 mg per day.

The ML-236B carboxylic acid derivatives (I) may be formulated to various preparations for administration by any conventional methods in analogy with other known antihyperlipemic agents such as Clofibrate, Sinfibrate and the like.

Then, in another aspect of this invention, there is provided a pharmaceutical preparation which comprises as an active ingredient at least one of the ML-236B carboxylic acid derivatives (I). This preparation may naturally include any pharmaceutically acceptable carrier or excipient.

The preparation is desirably provided in the form preferable for absorption in gastrointestinal tracts. Tablets and capsules for oral administration are of a unit dosage form and may comprise conventional vehicles such as a binding agent such as syrup, gum arabic, gelatin, sorbit, tragacanth gum or polyvinylpyrrolidone; an excipient such as lactose, sucrose, corn starch, calcium phosphate, sorbitol or glycine; a glidant such as magnesium stearate, talc, polyethylene glycol or silica; a disintegrating agent such as potato starch; or a wetting agent such as sodium lauryl sulfate. Tablets may be coated by any methods well-known in the art. Liquid preparations for oral administration may be an aqueous or oily suspension, a solution, a syrup, an elixir and the like or they may be of any dried forms which may be re-dissolved in water or other suitable vehicles when applied. Such liquid preparations may comprise conventional additives such as a suspending agent such as sorbit syrup, methyl cellulose, glucose/sugar syrup, gelatin, hydroxyethyl cellulose, carboxymethyl cellulose, aluminum stearate gel or a hydrogenated edible fat; an emulsifying agent such as lecitin, sorbitan monooleate or gum arabic; a non-aqueous vehicle such as almond oil, fractionated coconut oil, oily ester, propylene glycol or ethanol; a preservative such as methyl p-hydroxybenzoate, propyl p-hydroxybenzoate or sorbic acid.

Injectable preparations are provided in a unit dosage ampoule or multiple dosage vessel with added preservatives. The preparations may be in the form of a suspension, a solution or an emulsion in oily or aqueous vehicles and also comprise formulating agents such as a suspending agent, a stabilizer and/or a dispersing agent. Alternatively, the active ingredient may be in the form of a powder which may be re-dissolved in a suitable vehicle, e.g., pyrogen-free, sterilized water when applied.

These preparations may contain not less than 0.1%, preferably 10–60% of the active ingredient, depending upon administration route. A unit dosage form of the preparation may preferably contain 50–500 mg of the active ingredient. The ML-236B carboxylic acid amino acid or metal salts when in an aqueous solution have a property of being lactonized to ML-236B in an acidic pH range. Therefore, an aqueous solution of the salts is preferably kept in a neutral to weakly alkaline pH range.

This invention will be more fully explained by way of the non-limiting Examples and Preparation Examples as shown hereinbelow.

EXAMPLE 1

Ethyl ML-236B carboxylate 10 g of ML-236B were dissolved with heating in 150 ml of ethanol and to the resulting solution were added 20 g of an acidic ion exchange resin (dry Dowex 50 W - $H^+$ form) and then stirring was effected at 60°–70° C. for 3 hours. After completion of the reaction, the resin was filtered off, the solvent was distilled off under reduced pressure and the residue was isolated and purified by silica gel (100 g) chromatography to give 6.1 g of the desired product and 3.1 g of the starting ML-236B.

Analysis for $C_{25}H_{40}O_6$ — Calcd.: C; 68.77%, H; 9.24%. Found: C; 68.82%, H; 9.31%.

NMR spectrum: $\delta$ ppm (CDCl$_3$), 4.20 (2H, quartet), 1.25 (3H, triplet).

IR spectrum: $\nu$ cm$^{-1}$ (liquid film) 1730.

EXAMPLE 2

Propyl ML-236B carboxylate

The same procedure as in Example 1 was repeated except that 2.5 g of ML-236B, 50 ml of n-propanol and 5 g of the acidic ion exchange resin were employed, thereby yielding 1.5 g of the desired product.

Analysis for $C_{26}H_{42}O_6$ — Calcd.: C; 69.30%, H; 9.40%. Found: C; 69.52%, H; 9.45%.

NMR spectrum: $\delta$ ppm (CDCl$_3$), 3.6–4.4 (4H, multiplet).

IR spectrum: $\nu$ cm$^{-1}$ (liquid film) 1732.

EXAMPLE 3

Isopropyl ML-236B carboxylate

The same procedure as in Example 1 was repeated except that 10 g of ML-236B, 200 ml of isopropanol and 20 g of the acidic ion exchange resin were employed, thereby yielding 6.5 g of the desired product and 3.6 g of the starting ML-236B.

Analysis for $C_{26}H_{42}O_6$ — Calcd.: C; 69.30%, H; 9.40%. Found: C; 69.83%, H; 9.30%.

NMR spectrum: $\delta$ ppm (CDCl$_3$), 5.10 (1H, multiplet), 1.25 (6H, doublet).

IR spectrum: $\nu$ cm$^{-1}$ (liquid film) 1725.

EXAMPLE 4

Hexyl ML-236B carboxylate

To a solution of 10 g of ML-236B carboxylic acid in 50 ml of n-hexylalcohol and 20 ml of benzene was added 0.5 ml of conc. sulfuric acid and the resulting mixture was stirred at room temperature for 16 hours. Then, the reaction mixture was neutralized with an aqueous solution of sodium hydrogencarbonate, washed with water, dried over anhydrous sodium sulfate and then the solvent was distilled off at a temperature of not more than 60° C. under reduced pressure. The residue was isolated and purified by a silica gel (100 g) chromatography to give 7.4 g of the desired product and 2.3 g of the starting ML-236B.

Analysis for $C_{29}H_{48}O_6$ — Calcd.: C; 70.69, H; 9.82. Found: C; 70.54, H; 10.12.

NMR spectrum: $\delta$ ppm (CDCl$_3$), 3.5–4.5 (4H, multiplet).

IR spectrum: $\nu$ cm$^{-1}$ (liquid film) 1735.

EXAMPLE 5

Benzyl ML-236B carboxylate

To a solution of 2.1 g of sodium ML-236B carboxylate in 10 ml of dimethylformamide were 10 mg of sodium iodide and 2 ml of benzyl chloride and the resulting mixture was left for 16 hours. Then, water was added to the reaction mixture and extraction was effected with ethyl acetate. The extract was washed with water and dried over anhydrous sodium sulfate and then the solvent was distilled off. The redidue was isolated and purified by silica gel (60 g) chromatography to give 2.2 g of the desired product.

Analysis for $C_{30}H_{42}O_6$ — Calcd.: C; 72.26, H; 8.49. Found: C; 72.45, H; 8.46.

NMR spectrum: $\delta$ ppm (CDCl$_3$), 5.18 (2H, singlet), 7.40 (5H, singlet).

IR spectrum: $\nu$ cm$^{-1}$ (liquid film) 1730.

EXAMPLE 6

4-Methylbenzyl ML-236B carboxylate

The same procedure as in Example 5 was repeated except that 2.0 g of sodium ML-236B carboxylate, 2 ml of 4-methylbenzyl chloride and 10 ml of dimethylformamide were employed, thereby yielding 2.3 g of the desired product.

Analysis for $C_{31}H_{44}O_6$ — Calcd.: C; 72.62, H; 8.65. Found: C; 72.50, H; 8.32.

NMR spectrum: $\delta$ ppm (CDCl$_3$), 2.30 (3H, singlet), 5.10 (2H, singlet), 7.40 (5H, singlet).

IR spectrum: $\nu$ cm$^{-1}$ (liquid film) 1730.

EXAMPLE 7

4-Methoxybenzyl ML-236B carboxylate

The same procedure as in Example 5 was repeated except that 2.0 g of sodium ML-236B carboxylate, 2.5 g of 4-methoxybenzyl chloride and 10 ml of dimethylformamide were employed, thereby yielding 2.2 g of the desired product.

Analysis for $C_{31}H_{44}O_7$ — Calcd.: C; 70.43, H; 8.39. Found: C; 70.81, H; 8.52.

NMR spectrum: $\delta$ ppm (CDCl$_3$), 3.75 (3H, singlet), 5.12 (2H, singlet), 6.80, 7.05 (4H, quartet).

IR spectrum: $\nu$ cm$^{-1}$ (liquid film) 1735.

EXAMPLE 8

4-Chlorobenzyl ML-236B carboxylate

The same procedure as in Example 5 was repeated exept that 1.0 g of sodium ML-236B carboxylate, 1.5 g of 4-chlorobenzyl chloride and 7 ml of dimethylformamide were employed, thereby yielding 1.3 g of the desired product.

Analysis for $C_{30}H_{41}O_6Cl$ — Calcd.: C; 67.58, H; 7.75. Found: C; 67.71, H; 7.77.

NMR spectrum: $\delta$ ppm (CDCl$_3$), 5.20 (2H, singlet), 7.38 (4H, singlet).

IR spectrum: $\nu$ cm$^{-1}$ (liquid film) 1730.

EXAMPLE 9

Phenacyl ML-236B carboxylate

A solution of 10.5 g of sodium ML-236B carboxylate and 6.3 g of phenacyl bromide in 50 ml of dimethylformamide was left at room temperature for 3 hours. Then, water was added to the reaction mixture and the resulting mixture was extracted with ethyl acetate. The extract was washed with water, dried over anhydrous sodium sulfate and then the solvent was distilled off. The residue was isolated and purified by silica gel (150 g) chromatography to give 11.3 g of the desired product as a colorless oily substance.

Analysis for $C_{31}H_{42}O_7$ — Calcd.: C; 70.69, H; 8.04. Found: C; 70.45, H; 8.21.

NMR spectrum: $\delta$ ppm (CDCl$_3$), 5.44 (2H, singlet), 7.4–8.2 (5H, multiplet).

IR spectrum: $\nu$ cm$^{-1}$ (liquid film) 1745, 1725, 1710.

EXAMPLE 10

4-Bromophenacyl ML-236B carboxylate

The same procedure as in Example 9 was repeated except that 1.0 g of sodium ML-236B carboxylate, 1 g of p-bromophenacyl bromide and 10 ml of dimethylformamide were employed to give 1.4 g of the desired product.

Analysis for $C_{31}H_{41}O_7Br$ — Calcd.: C; 61.48, H; 6.82. Found: C; 61.20, H; 7.01.

NMR spectrum: $\delta$ ppm (CDCl$_3$), 5.40 (2H, singlet), 7.45–8.0 (4H, multiplet).

IR spectrum: $\nu$ cm$^{-1}$ (liquid film) 1730, 1710.

EXAMPLE 11

4-Methylphenacyl ML-236B carboxylate

The same procedure as in Example 9 was repeated except that 1.0 g of sodium ML-236B carboxylate, 1.0 g of 4-methylphenacyl bromide and 10 ml of dimethylformamide were employed to give 1.1 g of the desired product.

Analysis for $C_{32}H_{44}O_7$ — Calcd.: C; 71.08, H; 8.20. Found: C; 71.38, H; 8.46.

NMR spectrum: $\delta$ ppm (CDCl$_3$), 2.46 (3H, singlet), 5.42 (2H, singlet), 7.5–8.2 (4H, multiplet).

IR spectrum: $\nu$ cm$^{-1}$ (liquid film) 1745, 1730, 1710.

EXAMPLE 12

4-Methoxyphenacyl ML-236B carboxylate

The same procedure as in Example 9 was repeated except that 1.0 g of sodium ML-236B carboxylate, 1.2 g of 4-methoxyphenacyl bromide and 10 ml of dimethylformamide were employed to give 0.9 g of the desired pruduct.

Analysis of $C_{32}H_{44}O_8$ — Calcd. C; 69.04, H; 7.97. Found: C; 69.20, H; 8.19.

NMR spectrum: $\delta$ ppm (CDCl$_3$), 3.81 (3H, singlet), 5.45 (2H, singlet), 6.6–8.0 (4H, multiplet).

IR spectrum: $\nu$ cm$^{-2}$ (liquid film) 1740, 1725, 1710.

EXAMPLE 13

Methyl ML-236B carboxylate

A mixture of 9.75 g of ML-236B and 225 ml of a 0.1 N aqueous NaOH solution was heated on a water bath at 80°–90° C. for 1 hour while occasionally shaken. After 1 hour, undissolved ML-236B was filtered off, the filtrate was made acidic with HCl under ice-cooling and extracted with ethyl acetate. The extract was well washed with a saturated aqueous NaCl solution and dried over Na$_2$SO$_4$. The dried ethyl acetate extract was treated with an etheral solution of diazomethane. The solvent was distilled off and the residue was purified by silica gel chromatography to give 6.1 g of the desired product as colorless oily substance. Yield: 58%.

$[\alpha]_D^{25} = +202.55$ (c = 1% ethanol).

NMR spectrum: $\delta$ ppm (CDCl$_3$), 3.7 (3H, singlet).

IR spectrum: $\nu$ cm$^{-1}$ (liquid film) 1725, 3450.

Mass spectrum (molecular weight 422.54): M$^+$ 422.

EXAMPLE 14

Ethyl ML-236B carboxylate

A mixture of 30.9 g of ML-236B and 775 ml of a 0.1 N aqueous NaOH solution was heated on a water bath at 80°–90° C. for 1 hour, while occasionally shaken. The ML-236B gradually dissolved. After 1 hour, undissolved ML-236B was filtered off, the filtrate was freeze-dried to give 27.0 g of sodium ML-236B carboxylate as white powders.

5.0 g (0.01 mol) of the substance thus obtained were added to 30 ml of absolute ethanol to form a suspension. Dry hydrogen chloride gas was bubbled into the suspension under ice-cooling, whereupon NaCl was separated out. The solvent was dissolved off at a low temperature and the residue was dissolved in benzene. The resulting solution was washed with an aqueous sodium hydrogencarbonate solution and then with a saturated aqueous sodium chloride solution and dried over Na$_2$SO$_4$. The solvent was distilled off and the residue was purified by silica gel column chromatography to give 2.0 g of the desired product as colorless oily substance. Yield: 45.87%

$[\alpha]_D^{25} = +188.25$ (c = 1%, ethanol).

NMR spectrum: $\delta$ ppm (CDCl$_3$), 4.14 (2H, quartet), 1.25 (3H, triplet).

IR spectrum: $\nu$ cm$^{-1}$ (liquid film): 1725, 3450.

Mass spectrum (molecular weight 436.57): M$^+$ 436.

EXAMPLE 15

Ethyl ML-236B carboxylate

To a mixture of 1.0 g (0.0025 mol) of ML-236B and 15 ml of absolute ethanol were added several drops of acetyl chloride and stirring was continued at room temperature overnight. The solvent was distilled off and the residue was purified by silica gel column chromatography to give 0.3 g of the desired product as colorless oily substance. Yield: 26.85%

$[\alpha]_D^{25} = +188.25$ (c = 1%, ethanol).

NMR spectrum: $\delta$ ppm (CDCl$_3$), 4.14 (2H, quartet), 1.25 (3H, triplet).

IR spectrum: $\nu$ cm$^{-1}$ (liquid film) 1725, 3450.

Mass spectrum (molecular weight 436.57): M$^+$ 436.

EXAMPLE 16

Isopropyl ML-236B carboxylate

To 20 ml of absolute isopropanol were added 3.0 g (0.0069 mol) of sodium ML-236B carboxylate to form a suspension. Dry hydrogen chloride gas was bubbled into the suspension under ice-cooling and stirring. NaCl was separated. The solvent was distilled off at a low temperature and the residue was dissolved in benzene. The solution was washed with an aqueous sodium hydrogen-carbonate solution and dried over $Na_2SO_4$. The solvent was distilled off and the residue was purified by silica gel column chromatography to give 1.6 g of the desired product as colorless oily substance. Yield: 51.02%

$[\alpha]_D^{25} = +178.24$ (c = 1%, ethanol).

NMR spectrum: $\delta$ ppm ($CDCl_3$), 5.08 (1H, multiplet), 1.25 (6H, doublet).

IR spectrum: $\nu$ cm$^{-1}$ (liquid film) 1725, 3450.

Mass spectrum (molecular weight 450.60): M$^+$ 450.

EXAMPLE 17

Isopropyl ML-236B carboxylate

To 30 ml of absolute isopropanol were added 3.9g (0.01 mol) of ML-236B and several drops of acetyl chloride and the resulting mixture was heated to 50° C. for several minutes. Then, the solvent was distilled off and the residue was purified by silica gel column chromatography to give 2.6 g of the desired product as colorless oily substance. Yield: 57.78%

$[\alpha]_D^{25} = +178.24$ (c = 1%, ethanol).

NMR spectrum: $\delta$ ppm ($CDCl_3$), 5.08 (1H, multiplet), 1.25 (6H, doublet).

IR spectrum: $\nu$ cm$^{-1}$ (liquid film) 1725, 3450.

Mass spectrum (molecular weight 450.60): M$^+$ 450.

EXAMPLE 18 n-Butyl ML-236B carboxylate

To 50 ml of a 1% aqueous sodium hydroxide solution were added 10.0 g (0.026 mol) of ML-236B and a complete solution was formed with heating and shaking. Then, the solution was adjusted to pH 4 with 1 N hydrochloric acid under ice-cooling. Immediately after the adjustment, the solution was extract twice with ethyl acetate and the combined extracts were dried over sodium sulfate. The ethyl acetate was distilled off and the residue dissolved in n-butanol. To the solution was bubbled dry hydrogen chloride gas under ice-cooling and stirring for 10 minutes. The reaction mixture was washed with an aqueous sodium hydrogencarbonate solution and a saturated aqueous sodium chloride solution. The n-butanol was distilled off under reduced pressure and the residue was dissolved in benzene and then subjected to silica gel column chromatography to give 4.9 g of the desired product as colorless oily substance. Yield: 41.21%

Analysis for $C_{27}H_{44}O_6$ — Calcd.: C; 69.79, H; 9.55. Found: C; 69.40, H; 9.45.

$[\alpha]_D^{25} = +207.44$ (c = 1%, ethanol).

NMR spectrum: $\delta$ ppm ($CDCl_3$), 4.13 (5H, triplet).

IR spectrum: $\nu$ cm$^{-1}$ (liquid film) 1725, 3450.

Mass spectrum (molecular weight 464.62): M$^+$ 464.

EXAMPLE 19 n-Butyl ML-236B carboxylate

To 100 ml of n-butanol were added 13 g (0.033 mol) of ML-236B and a little amount of acetyl chloride and the resulting mixture was stirred at room temperature. Formation of the corresponding n-butyl ester was investigated occasionally by a thin layer chromatography and, whenever a poor formation was found, a further little amount of acetyl chloride was added and stirring was continued. When the starting material was scarcely observed, the reaction was ceased. A total amount of acetyl chloride was 1 g. The reaction mixture was washed with an aqueous sodium hydrogen-carbonate solution and a saturated aqueous sodium chloride solution and the n-butanol was distilled off under reduced pressure and the residue was subjected to silica gel column chromatography by the use of benzene as a developing agent to give 10.9 g of the desired product. Yield: 70.4%

$[\alpha]_D^{25} = +207.44$ (c = 1%, ethanol).

NMR spectrum: $\delta$ ppm ($CDCl_3$), 4.13 (3H, triplet).

IR spectrum: $\nu$ cm$^{-1}$ (liquid film) 1725, 3450.

Mass spectrum (molecular weight 464.62): M$^+$ 464.

EXAMPLE 20

Benzyl ML-236B carboxylate

A mixture of 39.0 g (0.1 mol) of ML-236B and 1 l. of a 0.1 N aqueous NaOH solution was heated on a water bath at 80°–90° C. for 1 hour with occasional shaking. The ML-236B gradually dissolved. After 1 hour, undissolved ML-236B was filtered off and the filtrate was made acidic with HCl under ice-cooling and extracted with ethyl acetate. The extract was well washed with a saturated aqueous sodium chloride solution and dried over sodium sulfate. This ethyl acetate extract was mixed with a separately prepared etheral solution of phenyl diazomethane. The solvent was distilled off and the residue was purified by silica gel column chromatography to give 8.6 g of the desired product as colorless oily substance. Yield: 17.27%

NMR spectrum: $\delta$ ppm ($CDCl_3$), 5.08 (2H, singlet), 7.34 (5H, singlet).

IR spectrum: $\nu$ cm$^{-1}$ (liquid film) 1725, 3450.

Mass spectrum (molecular weight 498.64): M$^+$ 498.

EXAMPLE 21

Sodium ML-236B carboxylate

A suspension of 39 g of ML-236B in an aqueous solution of sodium hydroxide (0.2 N, 500 ml) was stirred at 50° C. for 2 hours to form a substantially clear aqueous solution. A minor amount of the residual insolubles was filtered off and the filtrate freeze-dried to afford 40.2 g of ML-236B sodium salt.

UV spectrum (aqueous solution):

| $\lambda$ max (m$\mu$) | $D_{1cm}^{1\%}$ |
| --- | --- |
| 229.0 | 509 |
| 236.2 | 580 |
| 245.0 | 386 |

EXAMPLE 22

Calcium ML-236B carboxylate

To 1 l. of an aqueous solution containing 4.7 g of calcium hydroxide were added 50 g of ML-236B and the mixture was stirred at 50° C. for 2 hours. A whole solution containing the precipitates formed in situ was freeze-dried. The dried specimen (about 55 g) was suspended in 500 ml of ethyl acetate. The suspension was stirred at room temperature for 1 hour and precipitates were collected by filtration. The precipitates were further washed with 1 l. of ethyl acetate and dried under vacuum to afford 49.5 g of ML-236B calcium salt.

UV spectrum (aqueous solution):

| λ max (mμ) | $E_{1cm}^{1\%}$ |
|---|---|
| 229.0 | 516 |
| 236.2 | 596 |
| 245.0 | 393 |

EXAMPLE 23

Aluminum ML-236B carboxylate

A solution of 10 g of the ML-236B sodium salt produced in Production Example 1 in 100 ml of water was adjusted to pH 2 with hydrochloric acid and 100 ml of benzene was added thereto. After shaking, the benzene layer was recovered and concentrated to dryness. 8 g of the residue and 1.3 g of aluminum isopropoxide were dissolved in 200 ml of anhydrous benzene and the resulting solution was boiled under reflux for 2.5 hours. Then, the solvent was distilled off to leave 9.0 g of ML-236B aluminum salt.

UV spectrum (aqueous solution):

| λ max (mμ) | $E_{1cm}^{1\%}$ |
|---|---|
| 229.0 | 506 |
| 236.2 | 580 |
| 245.0 | 389 |

EXAMPLE 24

Lysine salt of ML-236B carboxylic acid

To a solution of 4.10 g of ML-236B carboxylic acid in 50 ml of ethanol was added an aqueous solution (5 ml) of 1.46 g of lysine. The resulting mixture was stirred at 60° C. for 30 minutes. Then, the solvent was distilled off under reduced pressure. To the residue were added 100 ml of ethyl acetate and stirring was effected at 70° C. Crystalline substance thus separated was recovered by filtration. Yield 4.7 g, m.p. 182° C.

Analysis for $C_{29}H_{48}N_2O_7$ — Calcd.: C, 71.58; H, 6.99; N, 2.89%. Found: C, 71.53; H, 7.08; N, 2.82%.

IR spectrum $cm^{-1}$ (Nujol): 3150, 2100, 1730, 1610, 1585, 1510, 1410, 1180, 1080, 545.

EXAMPLE 25

Arginine salt of ML-236B carboxylic acid

To a solution of 4.05 g of ML-236B carboxylic acid in 40 ml of tetrahydrofuran was added an aqueous solution (10 ml) of 1.75 g of arginine. Then, the same treatment as in Example 24 was conducted to yield 4.71 g of the desired product. m.p. 147° C.

Analysis for $C_{29}H_{48}N_4O_7$ — Calcd.: C, 59.77; H, 8.64; N, 9.62%. Found: C, 59.63; H, 8.72; N, 9.56%.

IR spectrum $cm^{-1}$ (Nujol): 3350, 3150, 1730, 1640, 1560, 1400, 1260, 1180, 1080, 830, 530.

Some preparation examples of this invention will be given below for illustration purpose only.

PREPARATION EXAMPLE 1

Capsule for Oral Administration

| Methyl ML-236B carboxylate | 250 mg |
|---|---|
| Lactose | 75 mg |
| Magnesium stearate | 15 mg |
| Total | 340 mg |

According to the above-defined formulation, ingredient powders were admixed and passed through a sieve of 60 mesh. Then, the sieved powder (340 mg) was packed into a No. 1 gelatin capsule to produce a capsule.

PREPARATION EXAMPLE 2

Injectable Preparation

ML-236B sodium salt was asceptically placed into a vial so that 250 mg of the sterilized salt was contained therein, asceptically freeze-dried and then sealed. It was admixed with 2 ml of physiological saline when applied, thereby forming an injectable preparation.

PREPARATION EXAMPLE 3

Capsule for Oral Administration

| ML-236B calcium salt | 250 mg |
|---|---|
| Lactose | 75 mg |
| Magnesium stearate | 15 mg |
| Total | 340 mg |

According to the above-defined formulation, ingredient powders were admixed and passed through a sieve of 60 mesh. Then, the sieved powder (340 mg) was packed into a No. 1 gelatin capsule to produce a capsule.

PREPARATION EXAMPLE 4

Injectable Preparation

ML-236B carboxylic acid.arginine salt was asceptically placed into a vial so that 100 mg of the sterilized salt was contained therein, asceptically freeze-dried and then sealed. It was admixed with 2 ml of physiological saline when applied, thereby forming an injectable preparation.

PREPARATION EXAMPLE 5

Capsule for Oral Administration

| Lysine salt of ML-236B carboxylic acid | 100 mg |
|---|---|
| Lactose | 75 mg |
| Magnesium stearate | 15 mg |
| Total | 190 mg |

According to the above-defined formulation, ingredient powders were admixed and passed through a sieve of 60 mesh. Then, the sieved powder (190 mg) was packed into a gelatin capsule to produce a capsule.

What is claimed is:

1. A compound having the formula

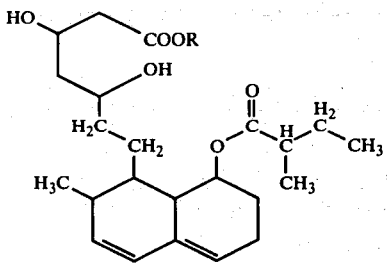

wherein R represents an alkyl group, a benzyl group optionally substituted with alkyl, alkoxy or halogen or a phenacyl group optionally substituted with alkyl, alkoxy or halogen; a group of $1/n$ M in which M represents a metal and n represents a valency of said metal; or a group of $AH^+$ in which A represents an amino acid.

2. A compound according to claim 1 wherein R is an alkyl group, a benzyl group optionally substituted with alkyl, alkoxy or halogen or a phenacyl group optionally substituted with alkyl, alkoxy or halogen.

3. A compound according to claim 2 wherein R is an alkyl group of 1 to 6 carbon atoms, a benzyl group optionally substituted with $C_1$-$C_2$ alkyl, $C_1$-$C_2$ alkoxy or halogen or a phenacyl group optionally substituted with $C_1$-$C_2$ alkyl, $C_1$-$C_2$ alkoxy or halogen.

4. A compound according to claim 2 wherein R is a methyl, ethyl, n-propyl, isopropyl, n-butyl, n-hexyl, benzyl, 4-methylbenzyl, 4-methoxybenzyl, 4-chlorobenzyl, phenacyl, 4-methylphenacyl, 4-methoxyphenacyl or 4-bromophenacyl group.

5. A compound according to claim 1 wherein R is a group of $1/n$ M in which M represents a metal and n is a valency of said metal.

6. A compound according to claim 5 wherein said metal is an alkali metal.

7. A compound according to claim 5 wherein said metal is an alkaline earth metal.

8. A compound according to claim 5 wherein said metal is aluminum.

9. A compound according to claim 5 wherein said metal is sodium or calcium.

10. A compound according to claim 1 wherein R is a group of $AH^+$ in which A is an amino acid.

11. A compound according to claim 10 wherein said amino acid is a basic amino acid.

12. A compound according to claim 10 wherein said amino acid is arginine, lysine, histidine, α,γ-diaminobutyric acid or ornithine.

13. A composition for the treatment of hyperlipemia which comprises as an active ingredient a compound of the formula

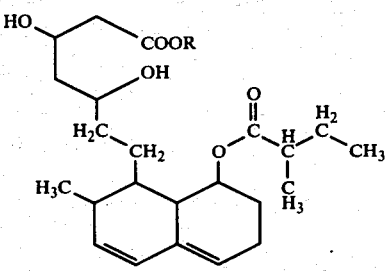

wherein R represents an alkyl group, a benzyl group optionally substituted with alkyl, alkoxy or halogen or a phenacyl group optionally substituted with alkyl, alkoxy or halogen; a group of $1/n$ M in which M represents a metal and n represents a valency of said metal; or a group of $AH^+$ in which A represents an amino acid and a pharmaceutically acceptable carrier.

14. A composition according to claim 13 wherein R is an alkyl group, a benzyl group optionally substituted with alkyl, alkoxy or halogen or a phenacyl group optionally substituted with alkyl, alkoxy or halogen.

15. A composition according to claim 13 wherein R is a group of $1/n$ M in which M represents a metal and n is a valency of said metal.

16. A composition according to claim 13 wherein R is a group of $AH^+$ in which A is an amino acid.

* * * * *